US00PP15386P2

(12) United States Plant Patent
Brown

(10) Patent No.: US PP15,386 P2
(45) Date of Patent: Nov. 30, 2004

(54) SWEET CHERRY TREE NAMED 'BROWN'

(50) Latin Name: *Prunus avium L.*
Varietal Denomination: Brown

(76) Inventor: Robert Brown, Blair Slack Rd., Wenatchee, WA (US) 98801

( * ) Notice: Subject to any disclaimer, the term of this patent is extended or adjusted under 35 U.S.C. 154(b) by 0 days.

(21) Appl. No.: 10/734,000

(22) Filed: Dec. 11, 2003

Related U.S. Application Data

(60) Provisional application No. 60/435,131, filed on Dec. 19, 2002.

(51) Int. Cl.[7] ..... A01H 5/00

(52) U.S. Cl. ..... Plt./181

(58) Field of Search ..... Plt./181

*Primary Examiner*—Kent Bell
(74) *Attorney, Agent, or Firm*—Stratton Ballew PLLC

(57) ABSTRACT

A new and distinct variety of sweet cherry, *Prunus avium* L., denominated 'Brown', which is a late-ripening mutation of the well-known 'Bing' variety. This mutation ripens 22 to 24 days after 'Bing' and is distinct from it, not only in maturity but also in other characteristics.

5 Drawing Sheets

Latin name of the genus and species of the plant claimed: *Prunus avium L.*
Variety denomination: 'Brown'.

STATEMENT REGARDING FEDERALLY SPONSORED RESEARCH OR DEVELOPMENT

None.

BACKGROUND OF THE INVENTION

The present invention relates to a new and distinct variety of sweet cherry tree, *Prunus avium L.*, which, though similar to its parent 'Bing' (not patented) in some characteristics, is decidedly different in maturity and other characteristics as described herein.

The new variety originated as a whole-branch mutation of a 'Bing' cherry tree growing in a cultivated orchard located at Wenatchee Heights, near Wenatchee, Wash., U.S.A., some time after the parent 'Bing' tree was planted in 1986. The mutated branch was first noticed by the inventor in 1994, who initially believed that some disease or other condition was causing the fruit on the mutated branch to ripe 22 to 24 days later than the rest of the tree.

In 1996, the inventor took scionwood from the original mutated branch and grafted it to two established 'Bing' cherry trees in an adjacent orchard. The established trees had been fruiting for three years. The fruit from the grafted trees is identical to that of the mutated branch of the original tree, thus establishing the trueness to type of the mutation. The claimed variety has further been shown to reproduce true to type over successive asexually propagated generations.

In 1997, 210 trees were budded at Wenatchee, Wash. U.S.A. These third-generation trees started fruiting in 2002.

BRIEF SUMMARY OF THE INVENTION

The new sweet cherry variety is similar, if not identical, to its parent 'Bing' in wood, leaf, bloom, and most fruit characteristics but is distinct from it in maturity, coloring pattern, firmness, and flavor. Because of its greater firmness, storage quality is longer than 'Bing'.

Interest in this new variety arises from the potentiality of extending the market for a 'Bing'-type cherry for at least one month.

DESCRIPTION OF THE PHOTOGRAPHS

The accompanying color photographs show typical tree, fruit, flower, and leaf specimens of the new sweet cherry tree variety and depict the color as near to true as it is reasonably possible to do in making a color illustration of this character. It should be noted that colors may vary with growing conditions and time of year, as well as with lighting conditions at the time the photographs are taken.

DETAILED DESCRIPTION OF THE VARIETY

Figure 1:
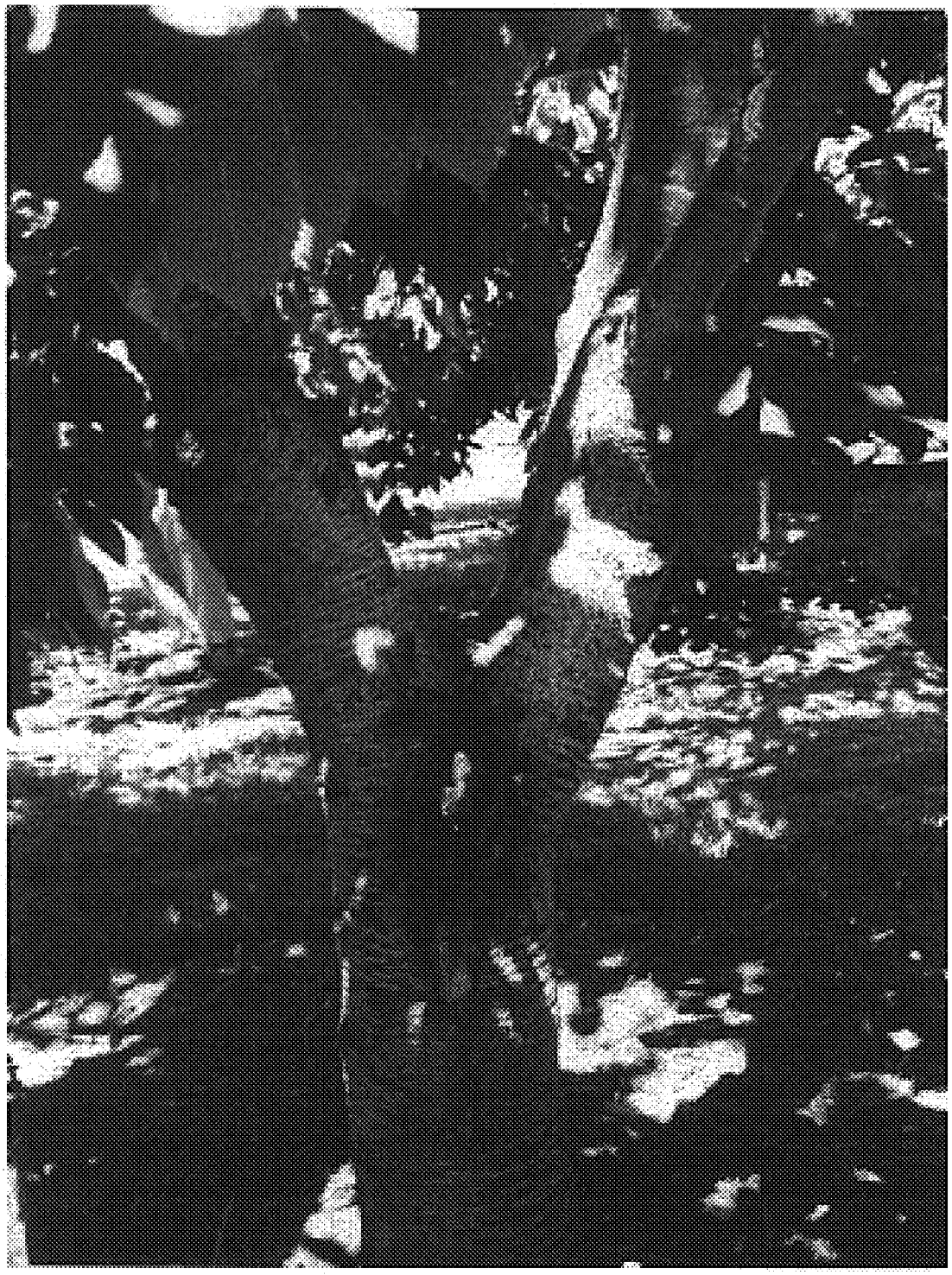
FIG. 1 is a photograph of the parent 'Bing' tree, showing the mutated branch.
Figure 2:
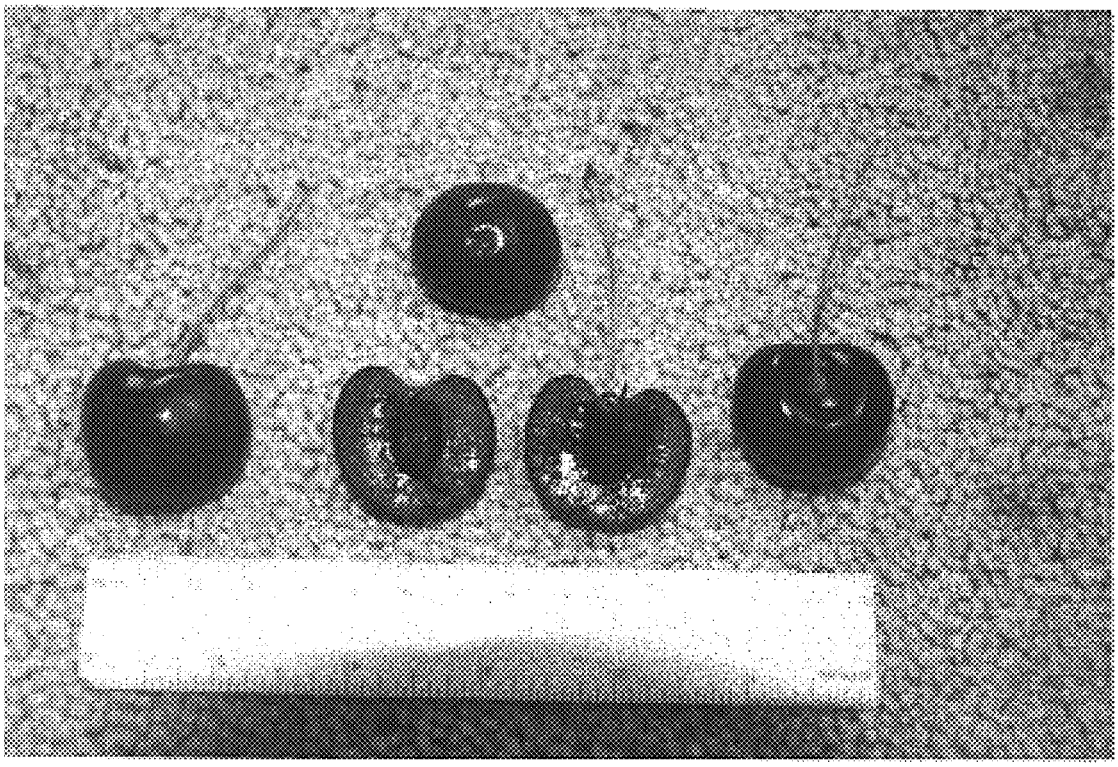
FIG. 2 is a close-up photograph of the fruit of the 'Brown' cherry tree in various aspects.
Figure 3:
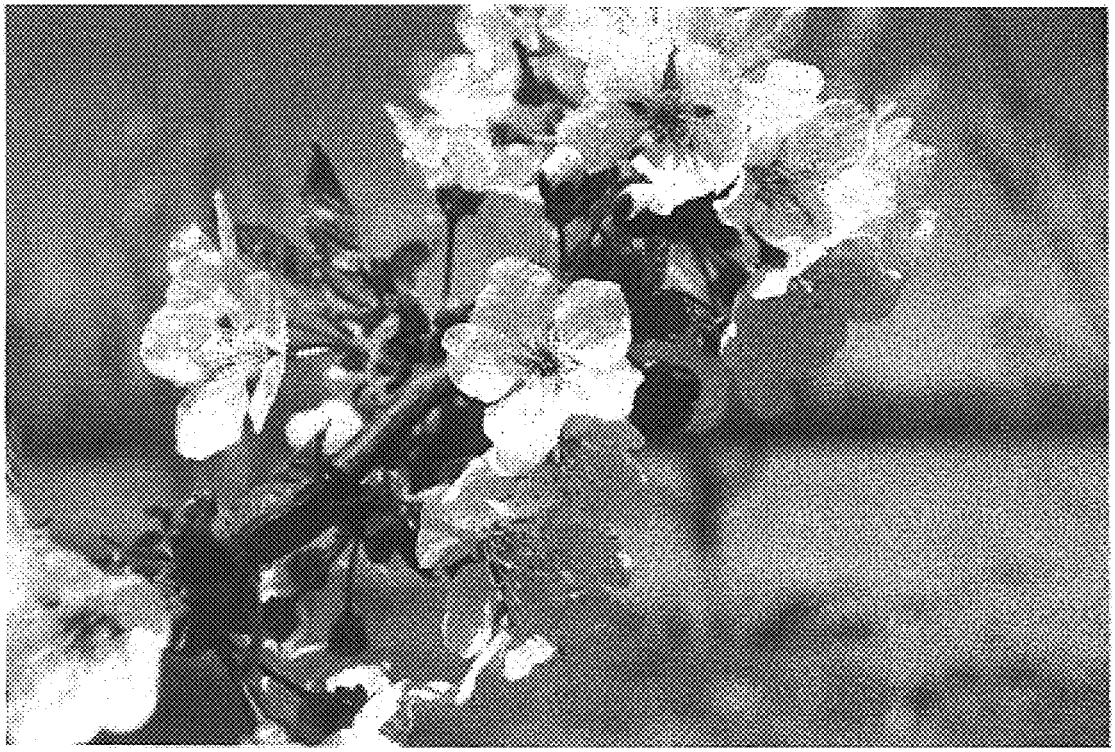
FIG. 3 is a photograph of the flowers of the 'Brown' cherry tree.
Figure 4:
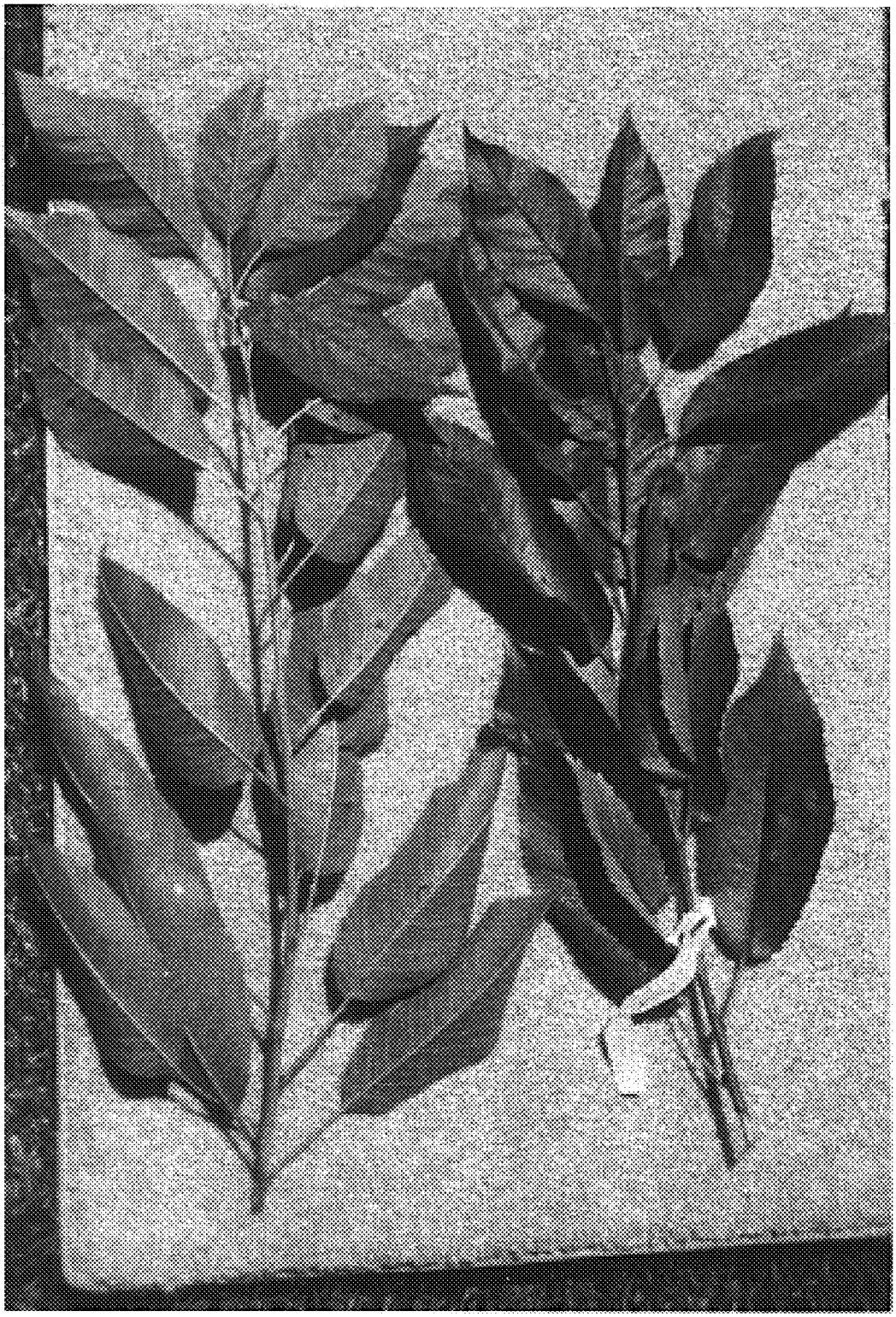
FIG. 4 is a photo of a vegetative shoot of the 'Brown' cherry tree, showing upper and lower leaf surfaces.
Figure 5:
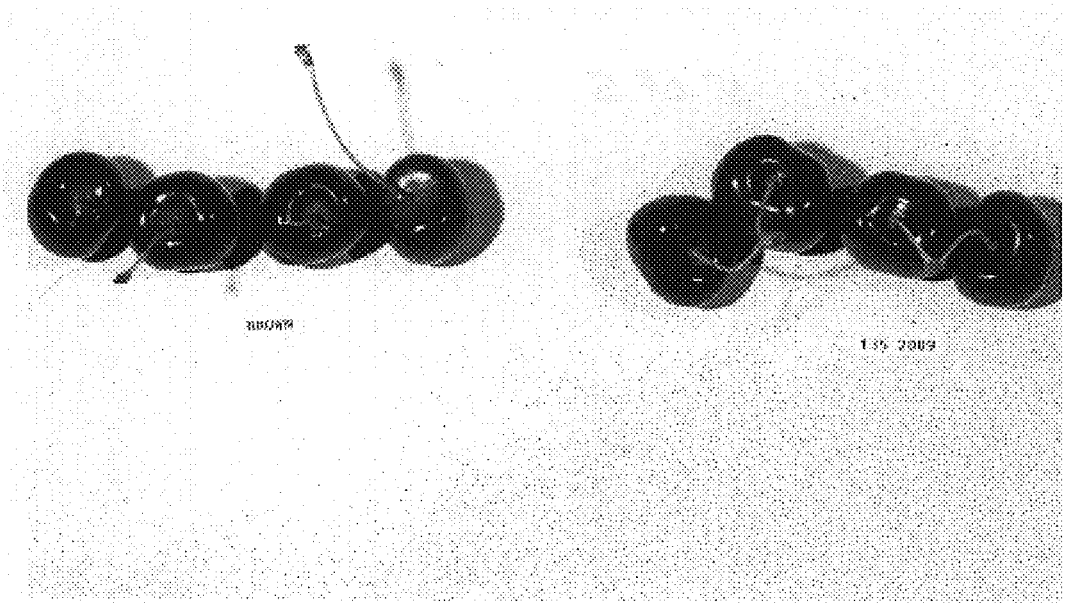
FIG. 5 is a comparison of the fruit of the 'Brown' cherry tree with Staccato™ '13S2009' (U.S. Patent applied for) (shown as "135 2009").

The following is a detailed botanical description of the new variety of cherry tree, based on observations made on the ten year old original branch mutation of an eighteen year old 'Bing' cherry tree located in a commercial orchard on Stemilt Hill, five miles west of Wenatchee, Wash., U.S.A. Color terminology (hue/value/chroma) is in accordance with the Munsell Book of Color, MacBeth Division, Kollmorgen Instruments Corp., 405 Little Britain Road, New Windsor, N.Y. 12553.

Scientific name: *Prunus avium* L., 'Brown' cultivar.
Parentage: Limb mutation of *Prunus avium* L., 'Bing'.
Tree:

*Size.*—Large, width 3.5 m, height 5.0 m, identical to 'Bing'.

*Vigor.*—Vigorous, annual growth approximately 45 cm.
*Branching habit.*—Upright, spreading.
*Density.*—Average for sweet cherry.
*Hardiness.*—Apparently hardy where tested (north central Washington state, USDA zone 5; identical to 'Bing').
*Productivity.*—Good, similar to 'Bing', approximately 150 lbs fruit per tree during 2003 growing season.
*Bearing habit.*—Annual, consistent.
*Shape.*—Pruned for commercial production, steep leader training, moderate to heavy pruning to produce large fruit.

Trunk:
*Size.*—25 cm in diameter at 30 cm from soil line.
*Bark texture.*—Typical sweet cherry: smooth, with vertical striations and horizontal lenticels.
*Bark color.*—Reddish brown (7.5 R 2/4).
*Lenticels.*—Elongated, 0.5×3 cm, about 2 cm apart vertically.

Branches:
*Size.*—Original 'Bing' tree, 20 cm diameter at 30 cm from crotch; mutated 'Brown' branch, 12.5 cm in diameter at 30 cm from point of origin.
*Texture.*—Typical of sweet cherry, smooth with vertical striations and horizontal lenticels.
*Habit.*—Upright to spreading.
*Color.*—Reddish brown (7.5 R 2/4).
*Current season shoot:*—0.5 cm×50 cm (length), smooth surface; Greenish brown (2.5 Y 4/4); lenticels sparse, approximately 1 per square cm, 0.5 mm in diameter, Light tan (2.5 Y 6/4).

Leaves: (Measurements are average of 10 mature leaves from upright shoots of the current season's growth).
*Size.*—Large, 15.8 cm long, 6.7 cm wide.
*Sheen.*—Glossy.
*Form.*—Lanceolate with acuminate tip.
*Petiole.*—3.0 to 3.5 cm long; 3 mm thick at base, brownish green (5 Y 5/8) along petiole groove; Olive green (2.5 GY 6/4) along lower surface.
*Margin.*—Somewhat irregularly serrate (teeth vary in length).
*Midvein.*—Medium, 2 mm thick at base; Olive green (2.5 GY 7/6), tapering to apex.
*Tip.*—Acuminate.
*Base.*—Oblate.
*Glands.*—Two in number, positioned alternatively; prominent, reniform in shape, dark purple in color (7.5 R 9/2); positioned on rim of petiole groove about 2 to 3.5 cm from base of leaf petiole.
*Stipules.*—Lacking.
*Color.*—Upwardly disposed surface, dark green (10 GY 3/6); downwardly disposed surface, medium green (7.5 GY 5/4).
*Texture.*—Smooth, with slight depression along veins.

Flower buds:
*Hardiness.*—Hardy.
*Size.*—Medium (2 mm diameter).
*Length.*—Medium (5 mm).
*Form.*—Long, conic.
*Color.*—White (partially open buds).
*Quantity.*—One to 5, average quantity 2 per node.

Flowers: Self-sterile. First bloom April 24 at Wenatchee Heights; Full bloom April 27, same as 'Bing'.
*Size.*—Medium-large, 30 to 35 mm in diameter when fully open.
*Color.*—White.
*Bloom count.*—Generally 3 per bud (same as 'Bing'), 5 to 8 buds per spur cluster.
*Petals.*—Quantity 5 per flower; average length 15 mm, width 12.5 mm, cupped slightly inward; apex round; base acute; margin smooth, non serrated; upper and lower surfaces white in color.
*Anthers.*—Large, yellow (5 Y 8.5/4).
*Pollen.*—Abundant, yellow (5 Y 8.5/12).
*Stamens.*—Filament length 10 mm.
*Pistils.*—One per flower.
*Pedicel.*—Medium length, 20 mm, diameter 1 mm; Green 5GY 5/6.
*Peduncle.*—Length 3 mm; diameter 4 mm; Brown 10YR 4/6.
*Bloom fragrance.*—Slight to none.
*Showiness.*—Medium, typical of most cherry flowers.

Fruit:
*Maturity when described.*—Eating ripe (19 to 21 degrees Brix) Aug. 5, 2002, at Wenatchee Heights, Wash.
*Date of first picking.*—Aug. 5, 2002.
*Date of last picking.*—Aug. 15, 2002.
*Size.*—Large, 29.76 to 31.35 mm (8½ to 9 row) transverse diameter; 23 to 25 mm apical diameter.
*Form.*—Uniform, symmetrical, mostly round to slightly reniform.
*Quantity.*—2 to 3 per cluster.
*Suture.*—Slightly raised and of darker color than the rest of the skin.
*Stem cavity.*—Medium to shallow, maximum depth 2 mm; breadth 10 mm shoulder to shoulder; characteristically lighter in color at base of stem (see 'skin').
*Base.*—Rounded.
*Apex.*—Rounded pistil point slightly indented.
*Stem.*—Rather thin, diameter 1.5 mm; length 29 mm; Green 5GY 5/6; closely adhering to flesh; susceptibility to cracking not known since rain is rare during this late season.
*Skin color.*—Deep purple (2.5 R 2/4) except around base of stem, where it is bright red (7.5 R 3/12). This is a unique feature of this variety, unlike its parent, 'Bing', or 'Staccato', a similar cherry ripening in the same season.
*Flesh color.*—Deep purplish red (5 R 3/4).
*Flesh texture.*—Extremely firm, firmer than 'Bing' or 'Staccato'. Firmness as measured by a Firmtech instrument on fully ripe fruit (±20 degrees Brix) averaged over 400 g/mm. 'Bing' picked at a similar maturity averages about 255 g/mm.
*Fibers.*—Few.
*Ripening uniformity.*—Moderately even (single harvest).
*Flavor.*—Sweet, low acid, milder than 'Staccato' and 'Bing'.
*Juice.*—Dark, similar to flesh in color (5 R 3/4).
*Aroma.*—Very slight.
*Eating quality.*—Very good.

Stone:
*Stone type.*—Flesh clings to pit, similar to 'Bing' and most other cherry varieties.
*Size.*—Medium, 11 mm long, 9 mm wide, 8 mm thick.
*Form.*—Oval, rounded, very smooth; helium small, apex round.
*Sides.*—Equal.
*Surface.*—Very smooth.

*Ventral edge.*—Wide, with slight wings on ridges converging basically and apically.

*Dorsal edge.*—Smooth, with narrow ridge from base to apex.

*Color.*—Light tan (10 YR 8/4) when dry.

*Tendency to split.*—None.

Keeping quality: Excellent, at least 30 days in refrigerated storage.

Resistance to insects and diseases: Similar to that of 'Bing' and other sweet cherries. No special resistances observed.

Shipping quality: Excellent, due to its extreme firmness.

Variance in botanical details: The cherry tree and its fruit as described herein will vary due to climate and growing conditions. The present description refers to its characteristics as grown at Wenatchee Heights, near Wenatchee, Wash. Comparisons are with 'Bing' and 'Staccato' grown at the same location and with which the new variety is most likely to be compared.

It is claimed:

1. A new and distinct variety of cherry tree as described and illustrated herein, characterized by its maturity 22 to 24 days later than 'Bing' and by a lighter-colored circle around the base of the stem, unlike its parent 'Bing', or the late-maturing variety 'Staccato' with which it matures.

* * * * *